United States Patent [19]

Farr

[11] Patent Number: 5,019,088
[45] Date of Patent: May 28, 1991

[54] OVOID ATHERECTOMY CUTTER
[75] Inventor: Andrew F. Farr, Spring Valley, Calif.
[73] Assignee: Interventional Technologies Inc., San Diego, Calif.
[21] Appl. No.: 432,512
[22] Filed: Nov. 7, 1989
[51] Int. Cl.⁵ .................................................. A61B 17/32
[52] U.S. Cl. ..................................... 606/159; 606/180
[58] Field of Search ............... 606/159, 160, 161, 170, 606/180, 80, 81; 604/22; 15/104.09, 104.16

[56] References Cited

U.S. PATENT DOCUMENTS

| | | | |
|---|---|---|---|
| 2,729,210 | 1/1956 | Spencer | 128/2 |
| 2,749,909 | 6/1956 | Ullery et al. | 128/2 |
| 3,320,957 | 5/1967 | Sokolik | 606/180 |
| 3,512,519 | 10/1967 | Hall | 128/2 |
| 3,605,721 | 9/1971 | Hallac | 128/2 B |
| 3,815,604 | 6/1974 | O'Malley et al. | 128/305 |
| 3,990,453 | 11/1976 | Douvas et al. | 128/305 |
| 4,273,128 | 6/1981 | Lary | 128/305 |
| 4,320,762 | 3/1982 | Bentov | 128/343 |
| 4,441,509 | 4/1984 | Kotsifas et al. | 128/757 |
| 4,445,509 | 5/1984 | Auth | 606/180 X |
| 4,589,412 | 5/1986 | Kensey | 128/305 |
| 4,598,710 | 7/1966 | Kleinberg et al. | 128/318 |
| 4,610,662 | 9/1986 | Weikl et al. | 604/53 |
| 4,627,436 | 12/1986 | Leckrone | 128/303.1 |
| 4,631,052 | 12/1986 | Kensey | 604/22 |
| 4,636,195 | 1/1987 | Wolinsky | 604/53 |
| 4,640,296 | 2/1987 | Schnepp-Pesch et al. | 128/754 |
| 4,646,738 | 3/1987 | Trott | 128/305 |
| 4,653,496 | 3/1987 | Bundy et al. | 128/305 |
| 4,655,217 | 4/1987 | Reed | 128/305 |
| 4,655,771 | 4/1987 | Wallsten | 623/1 |
| 4,664,112 | 5/1987 | Kensey et al. | 128/341 |
| 4,665,918 | 5/1987 | Garza et al. | 128/343 |
| 4,669,469 | 6/1987 | Gifford, III et al. | 128/305 |
| 4,679,557 | 7/1987 | Opie et al. | 128/305 |
| 4,685,458 | 8/1987 | Leckrone | 128/303 |
| 4,686,982 | 8/1987 | Nash | 128/305 |
| 4,690,140 | 9/1987 | Mecca | 128/305 |
| 4,696,667 | 9/1987 | Masch | 604/22 |
| 4,708,147 | 11/1987 | Haaga | 128/753 |
| 4,728,319 | 3/1988 | Masch | 604/22 |
| 4,732,154 | 3/1988 | Shiber | 128/305 |
| 4,754,755 | 7/1988 | Husted | 128/305 |
| 4,765,332 | 8/1988 | Fischell et al. | 128/305 |
| 4,857,045 | 8/1989 | Rydell | 604/22 |
| 4,887,613 | 12/1989 | Farr et al. | 606/159 |
| 4,895,166 | 1/1990 | Farr et al. | 606/159 X |
| 5,757,826 | 7/1988 | Abdulhay | 128/757 |

OTHER PUBLICATIONS

Banning G. Lary, M.D., Method for Increasing the Diameter of Long Segments of the Coronary Artery, *The American Surgeon*, Jan., 1966, vol. 32, No. 1, pp. 33-35.

Banning G. Lary, M.D. and Roger W. Sherman, M.D., A Method for Creating a Coronary-Myocardial Artery, *Surgery, St. Louis*, Jun., 1966, vol. 59, No. 6, pp. 1061-1064.

Banning G. Lary, M.D., Coronary Artery Incision and Dilation, *Archives of Surgery*, Dec. 1980, vol. 115, pp. 1478-1480.

*Primary Examiner*—Michael H. Thaler
*Attorney, Agent, or Firm*—Nydegger & Associates

[57] ABSTRACT

A rotatable atherectomy cutter for removing obstructive tissue from a body vessel includes a hollow cylindrical base having an outer wall, a hollow cylindrical guide tip coaxially distanced from the base for slidably receiving a guide wire and a pair of dismetrically opposed blades each having a distal end and a proximal end. The distal end of each blade is connected to the guide tip and the proximal end connected to the base for alternately cutting the tissue with a first cutting edge and a second cutting edge longer than the first cutting edge. The proximal end of each blade is connected to an ovoid portion formed in the base for allowing the second cutting edge of the blade to extend beyond the outer diameter of the cylindrical base to cut a diameter of tissue larger than the diameter of the base. The base includes a straight wall portion connecting the pair of blades to establish the first cutting edge on each of the blades. The blades are inclined to the longitudinal axis of the cutter at an angle in the range of between thirty 30) and seventy (70) degrees and are preferably made of stainless steel. Also included is a mechanism for removing debris through an opening in the top of the base. The ovoid portion extends the second cutting edge of the blades beyond the outer wall a distance of approximately five (5) to ten 10) percent of the diameter of the base.

16 Claims, 2 Drawing Sheets

OVOID ATHERECTOMY CUTTER

FIELD OF THE INVENTION

This invention relates generally to rotary cutting devices. More specifically, the present invention relates to devices which are useful for cutting and removing obstructive tissue from the lumen of a body vessel. This invention is particularly, but not exclusively, suited for use as a cutting device in an atherectomy procedure where the opening to be cut through the obstructive tissue needs to be slightly larger than the cross-sectional dimensions of the basic structure of the cutting device so fluid can flow around and past the cutting device.

BACKGROUND OF THE INVENTION

A number of various means and procedures have been developed in recent years to remove obstructions to clear or open occluded arteries in order to restore the necessary circulation through the body. One approach is the so-called coronary "bypass" operation which requires a large incision into the body to open the chest cavity. This procedure is fairly traumatic to the body, and is quite drastic. Thus, other approaches for removing obstructions have been developed.

One alternate approach is the use of well known angioplasty procedures. A catheter is inserted through a small incision into the body through an artery to the site of the obstruction. The catheter incorporates a balloon to open the vessel by flattening the obstructive tissue against the vessel wall. With the angioplasty procedures, however, the obstructive tissue causing the occlusion remains in situ after the procedure is performed. Thus, while the problem may be alleviated, it is not eliminated. Also, there remains the real probability there will be a restenosis.

Another approach is the use of atherectomy procedures in which a catheter inserted into the artery includes a cutter head. Obstructive tissue causing the occlusion in the vessel is excised by the cutter from the lumen of the vessel. As should be readily apparent, the instruments used for this procedure incorporate precisely designed miniature cutting devices. Further, the devices require special fabrication and design considerations to allow satisfactory operation within the lumen of a vessel. Specifically, both the cutting device itself and its attendant drive elements which are inserted into the vessel with the cutting device must be miniaturized.

Several atherectomy related devices have been previously disclosed. Exemplary of such devices is U.S. Pat. No. 4,754,755 to Husted which discloses a catheter with a cylindrical rotary blade that is used to clear arterial obstructions. Another device is that disclosed in U.S. Pat. No. 4,273,128 to Lary for a coronary cutting and dilating instrument. It includes a balloon in combination with radially extending knife blades to permit incision and immediate dilation of the artery.

For each of the devices disclosed in these references, however, the effective cutting area of the blade of the device is limited. This is so because, in these conventional devices, the cutting action of the rotating blade does not extend beyond the periphery of the tubular structure or sheath which is used to feed the rotating blade through the artery or vessel. Consequently, the effective cutting capability of the blade inside a vessel is limited to a diameter which is equal to or less than the diameter of the blade. A diameter of cutting action which is greater than that of the blade is desired, however, to allow the cutter and its attendant sheaths or catheters to advance properly through the obstructive tissue, and to prevent the device from getting stuck in the vessel. Further, it is desirable that the cutting device not occlude fluid flow through the vessel, either when it is operational or when it is inoperative. Fluid should be able to flow around and past the cutting device at all times. Thus, there is a need for a cutter which has the capacity for cutting extended diameters. Accordingly, the present invention recognizes the need for an atherectomy cutter whose effective cutting action diameter extends beyond its base and attendant basic diameters to increase the cutting effectiveness of the device.

It is thus an object of the present invention to provide a cutter for an atherectomy device which has expanded cutting action when it is rotated inside the lumen of a body vessel. Another object of the present invention is to provide an atherectomy device which can be operatively positioned within the lumen as required to excise obstructive tissue from inside the lumen of a body vessel. Yet another object of the present invention is to provide a cutting device which allows fluid flow through the vessel around and past the cutting device. Still another object of the present invention is to provide an atherectomy device which can be effectively advanced during the cutting of obstructive tissue from the inside of a body vessel. Yet another object of the present invention is to provide an atherectomy device which is cost effective in its relative ease of use and manufacture.

SUMMARY OF THE INVENTION

A preferred embodiment of the rotatable atherectomy cutter comprises a hollow cylindrical base, a hollow cylindrical guide tip coaxially distanced from the base, and a pair of narrow blades connected between the base and the tip for establishing a first cutting edge and a second edge, the second cutting edge being longer than the first cutting edge. Also included is an ovoid portion being formed on the base located at the proximal end of each blade for connecting the blade to the base so that the second edge of each blade extends beyond the maximum diameter of the base. A preferred embodiment includes a straight wall portion connecting the pair of blades together to establish the first cutting edge on each of the blades. The first cutting edge in the preferred embodiment does not extend beyond the diameter of the base. The second cutting edge extends beyond the diameter of the base by an amount equivalent to between five (5) to ten (10) percent of the diameter of the base. The blades are inclined to the longitudinal axis of the cutter at an angle in the range of between thirty (30) to seventy (70) degrees. Also included is a guide wire insertable through the base and tip for guiding the cutter along the wire through the vessel. In a preferred embodiment, further, the first cutting edge of each blade faces in the first direction, and the second cutting edge faces in a second direction opposite the first direction.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 4 is a front view of the atherectomy cutter of the present invention;

DESCRIPTION OF THE PREFERRED EMBODIMENTS

Figure 1:
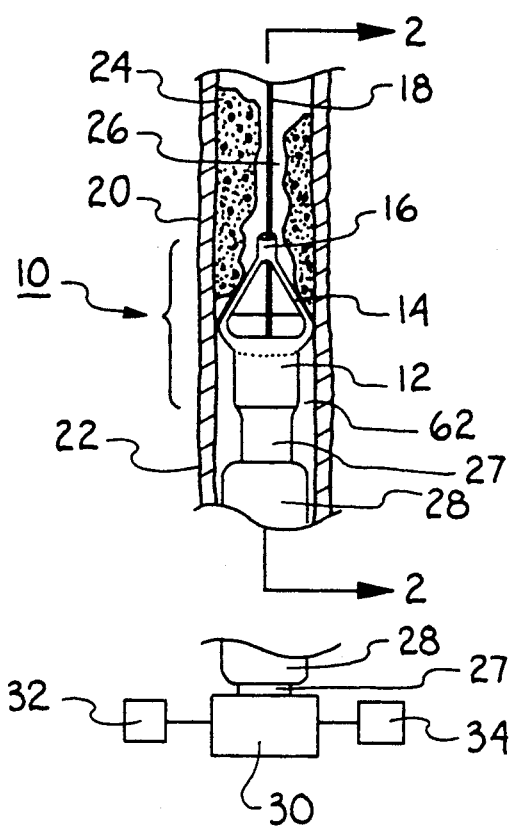
FIG. 1 is a partial cross-sectional view of a body vessel with the atherectomy cutter of the present invention shown positioned in the lumen of the vessel against obstructive tissue.

Referring initially to FIG. 1, there is shown an atherectomy cutter of the present invention, generally designated as 10, as seen in its operational environment. Specifically, cutter 10 comprises a hollow cylindrical base 12 having a pair of diametrically opposed blades 14 attached thereto joined at guide tip 16. Guide tip 16 is cylindrical and hollow, is of a diameter less than base 12, and is coaxially distanced from the cylindrical base 12 for slidably receiving a guide wire 18 for guiding the cutter. Cutter 10 is shown positioned inside vessel 20 having vessel wall 22, with obstructive tissue 24 occluding the lumen 26 of body vessel 20. Body vessel 20 is typically an artery, but can be other body vessels which may contain some obstructive tissue in the lumen thereof which is to be removed. Base 12 of cutter 10 is rotatably coupled to a rotatable torque tube 27 typically contained within a hollow sheath 28. Sheath 28 is a tubular structure used to cover torque tube 27 and which feeds the cutter 10 through the vessel. The sheath 28 and the covered torque tube 27 are coupled to a controller 30 having a drive means 32 for operatively causing rotation of torque tube 27 and thus cutter 10. Suction means 34 is also coupled to torque tube 27 to draw cuttings and other debris created by the action of the cutter 10 through the hollow base 12 into the torque tube. Debris and other unwanted matter can thus be removed from the lumen 26 of the vessel 20, as will be more fully explained below. As further shown in FIG. 2, the blades 14 are rotatable about the guide wire 18 as the cutter 10 is fed along lumen 26 of vessel 20.

Figure 3:
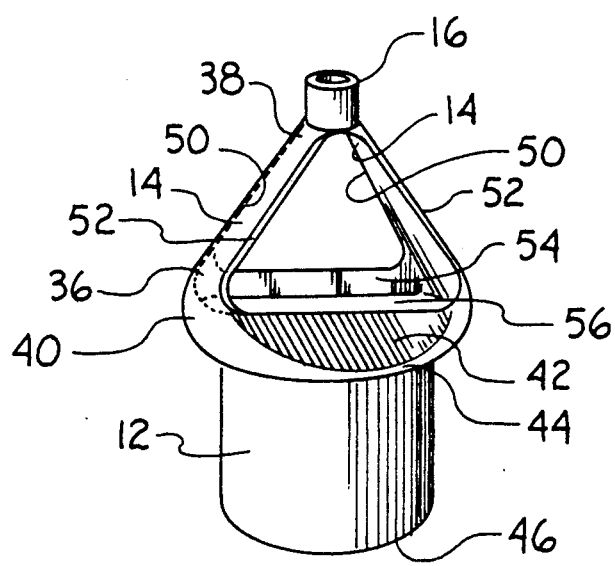
FIG. 3 is a perspective view of the atherectomy cutter of the present invention.
Figure 1:
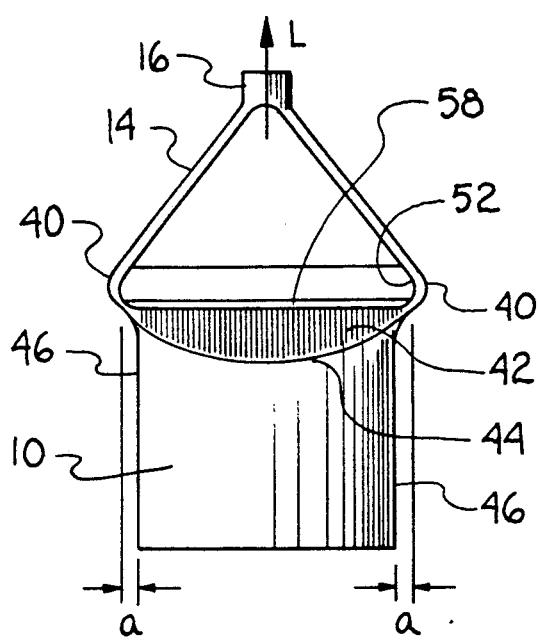
Figure 5:
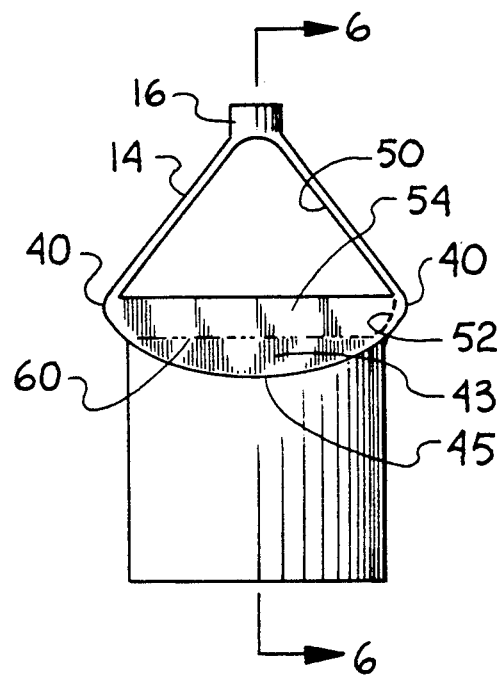
FIG. 5 is a rear view of the atherectomy cutter of FIG. 4.

Referring now to FIG. 3, there is shown a perspective view of cutte 10 showing in more detail the hollow, cylindrical base 12 and the pair of diametrically opposed blades 14 connected to hollow, cylindrical guide tip 16. Each blade 14 has a proximal end 36 and a distal end 38, with the distal end 38 being connected to hollow guide tip 16, and the proximal end being connected to an ovoid portion 40 of cylindrical base 12. Ovoid portion 40 is adjacent to a sloped surface portion 42 which is inclined from ridge 44 formed by the intersection of sloped surface 42 with the cylindrical outer wall 46 of hollow, cylindrical base 12. Each blade 14 has a first cutting edge 50, and a second cutting edge 52 on an opposite side of blade 14. First cutting edge 50 provides a cutting edge for cutting through obstructive tissue. Second cutting edge 52 also has a cutting edge, but it is longer than the first cutting edge 50. The cutter 12 also includes a straight wall portion 54 connected between the first cutting edge 50 of the pair of blades 14, adjacent opening 56.

Figure 6:
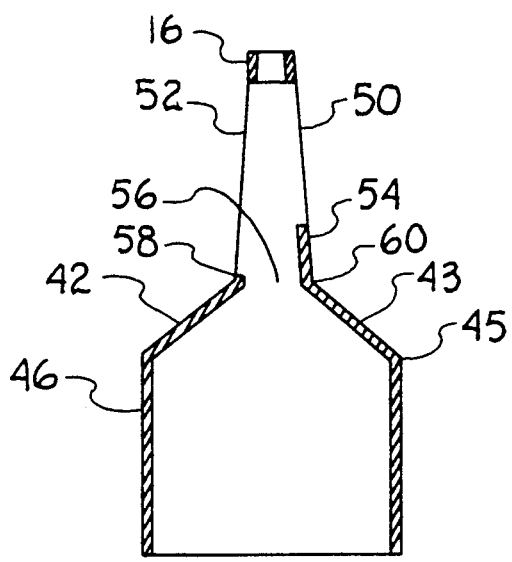
FIG. 6 is a cross-sectional view of the atherectomy cutter as seen along the line 6—6 in FIG. 5.

Referring now to FIGS. 4-7 there is shown front, back, side cross-sectional, and top views of the device illustrating further the structure of a preferred embodiment of the present invention. In particular, the ovoid portion 40 is shown in more detail in that it extends beyond the cylindrical outer wall 46 on opposed sides of the cylindrical, hollow base 12 by a distance represented as "a". In other words, the ovoid portion 40 of the cutter 10 serves to extend the second cutting edge 52, which is the longer cutting edge, beyond the outer diameter of the cylindrical outer wall 46. Also, it may be appreciated that the sloped surface 42 on the side of wall 46 slopes at an inclined angle to front rim 58 adjacent top opening 56, as shown in FIG. 6. It can further be appreciated with reference to FIGS. 5 and 6 that rear straight wall portion 54 includes a bend 60 at the intersection of straight wall portion 54 and inclined sloped surface 43 intersecting with ridge 45. As can be further appreciated with reference to FIG. 6, the rear straight wall 54 shortens the first cutting edge 50 so that it is shorter than the second cutting edge 52. It can also be seen in the embodiment shown that the pair of diametrically opposed blades 14 form an angle of approximately forty-five (45) degrees with respect to the longitudinal axis "L" of the device, as shown in FIG. 4. This slope or angle preferably ranges between approximately thirty (30) degrees to sixty (60) degrees, depending upon the particular results desired. This angle is important in determining forces related to cutting of the tissue.

Figure 7:
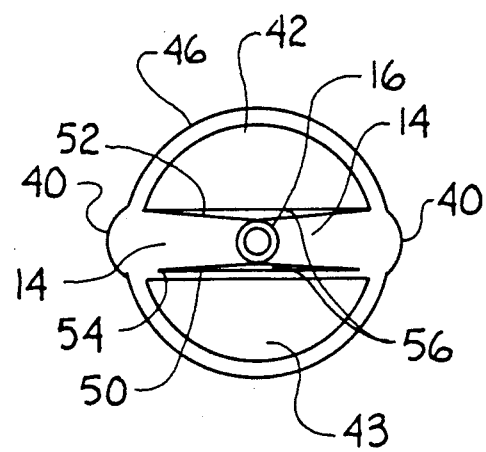
FIG. 7 is a top view of the atherectomy cutter in accordance with the present invention.

Referring further to FIG. 7, it can be appreciated from the top view of the cutter 10 that ovoid portion 40 can extend a sufficient distance to cause second cutting edge 52 to extend the desired amount beyond the diameter of the outside wall 46. The ovoid portion preferably extends the second cutting edge 52 beyond wall 46 a distance of up to approximately ten (10) percent of the diameter of the base 12. In addition, the straight wall portion 54 can be formed so as to connect with first cutting edge 50 at a more distal point to shorten the first cutting edge 50 even further, or at a more proximal point, to lengthen first cutting edge 50, as may be required depending upon the particular amount that first cutting edge 50 is desired to be shorter than second cutting edge 52. The further advantages and construction of the present invention are more fully appreciated by a description of the operation of the cutter as follows.

OPERATION

In operation, guide wire 18 is inserted through an incision in the body of the patient to introduce the guide wire 18 into the lumen 26 of body vessel 22. This then allows introduction of cutter 10 along the guide wire to the site of the obstructive tissue 24 which is to be excised. Once cutter 10 is positioned at the appropriate location, the cutter 10 is rotated at the appropriate speed by drive means 32, and suction means 34 is operatively engaged. In addition, typically there is fluid contained in the lumen of the vessel which assists operation of the cutter, and carries away tissue debris created by the cutter 10 as it cuts through obstructive tissue 24. The sheath 28 covers the torque tube as it is rotated within the sheath 28 for rotating the base 12 and cutting blades 14 in the desired direction. As the blades are rotated, first cutting edge 50 engages the obstructive tissue 24 and cuts away a tissue portion, and second cutting edge 52 being a longer cutting edge then cuts away further a portion of obstructive tissue 24. Since the second cutting edge 52 extends, by virtue of the ovoid portion 40, beyond the outer diameter of outer wall 46 of the cylindrical base 12, there is provided a passageway 62 as shown in FIG. 1 to allow the base 12 and sheath 28 to move along behind the blades 42 through the vessel more easily. In this manner, the base 12 and sheath 28, along with the presence of fluid as desired, is allowed to move freely through the lumen 26 of vessel 22.

As has been disclosed in a co-pending application Ser. No. 213,691, now U.S. Pat. No. 4,887,613 assigned to the same assignee as the present invention, it has been found that since first cutting edge 50 is shorter than second cutting edge 52, the second cutting edge 52 encounters more resistive tissue, the result of which operates to deflect cutter 10 off its longitudinal axis. This ensures a broader sweep of blades 14 to cut a channel having a diameter slightly greater than the diamater of base 12. The ovoid portion 40 further accentuates and enhances this action and provides increased effectiveness of cutting through tissue 24 and decreasing the possibility of the cutter 10 becoming stuck and seized up in the obstructive tissue 24.

Figure 2:
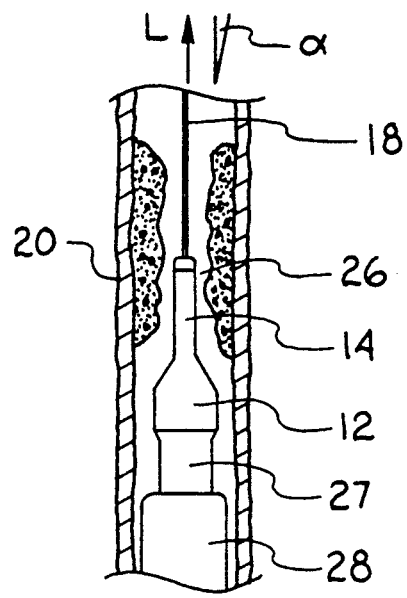
FIG. 2 is a cross-sectional view of the atherectomy cutter as seen along the line 2—2 in FIG. 1.

Also during the cutting action, an advantage of the rear straight wall 54 is that as cutter 10 is rotated, the rear straight wall portion 54 catches and deflects clippings of obstructive tissue, which have been cut away by second cutting edge 52, into the opening 56 to facilitate removal of cut away obstructive tissue. In addition, the sloped surfaces, 42, 43 further facilitate the movement of cutter 10 through obstructive tissue 24 and enhance the cutting action thereof. As shown in FIG. 2, the angle α of deflection of the cutter and the size of the opening made through the obstructive tissue 10 is affected by the respective length of first cutting edge 50 and second cutting edge 52, and the dimensions chosen for ovoid portion 40 and distance "a".

It will also be appreciated by cross referencing FIG. 1 and FIG. 2 that, regardless of the orientation of the cutter 10, there will be a narrow portion of the cutter 10 over the sloped surface 42 which will prevent cutter 10 from occluding vessel 20. This will be so even though ovoid portion 40 may be in contact with vessel wall 22. Thus, some fluid flow in vessel 20 can be maintained.

While the particular ovoid atherectomy cutter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

What is claimed is:

1. A rotatable atherectomy cutter for removing obstructive tissue from a body vessel, comprising:
    a hollow cylindrical base having an outer wall;
    a hollow cylindrical guide tip coaxially distanced from said base having a diameter less than the diameter of said base;
    a pair of narrow diametrically opposed blades, each having a distal end and a proximal end, each said proximal end being connected to said base and each said distal end being connected to said tip, each blade establishing a first cutting edge and a second cutting edge, each said second cutting edge being longer than each said first cutting edge; and
    an ovoid portion attached to said base and located at said proximal end of each said blades for connecting each of said blades to said base for allowing said second cutting edge to extend beyond the maximum diameter of said outer wall of said base.

2. A rotatably atherectomy cutter as recited in claim 1, wherein said first cutting edge does not extend beyond said outer wall.

3. A rotatable atherectomy cutter as recited in claim 1, wherein said second cutting edge extends beyond said outer wall by an amount equivalent to between five to ten percent of the diameter of said cylindrical base.

4. A rotatable atherectomy cutter as recited in claim 1, wherein said pair of blades are inclined to the longitudinal axis of said cutter at an angle in the range of between thirty and seventy degrees.

5. A rotatable atherectomy cutter as recited in claim 4, wherein said cutter is made of stainless steel.

6. A rotatable atherectomy cutter as recited in claim 1, further comprising a guide were insertable through said base and said tip for guiding said cutter along said wire through said vessel.

7. A rotatable atherectomy cutter as recited in claim 1, further comprising means coupled to said base for rotating said cutter, and suction means for removing debris through said hollow base.

8. A rotatable anterectomy cutter as recited in claim 1, wherein said first cutting edges of said blades each face in a first direction, and wherein said second cutting edges of said blades each face in a second direction opposite said first direction.

9. A rotatable atherectomy cuter for removing obstructive tissue from a body vessel, comprising:
    a hollow cylindrical base having an outer wall;
    a hollow cylindrical guide tip coaxially distanced from said base;
    a pair of substantially straight diametrically opposed blades extending from said guide tip, each said blade having a first edge and a second edge longer than said first edge; and
    an ovoid portion having a wall attached to said outer wall of said base and said blades for allowing said second edge of each said blade to extend beyond said outer wall of said base.

10. A rotatable atherectomy cutter as recited in claim 9, wherein said base includes a sloped surface adjacent said ovoid portion.

11. A rotatable atherectomy cutter as recited in claim 10, wherein said cutter is made of stainless steel.

12. A rotatable atherectomy cutter as recited in claim 11, wherein said ovoid portion extends said second cutting edge beyond said outer wall a distance of approximately five to ten percent of the diameter of said base.

13. A rotatable atherectomy cutter for removing obstructive tissue from a body vessel, comprising:
    a hollow cylindrical-shaped base having an outer wall;
    guide means coaxially distanced from said base for slidably receiving a guide wire;
    cutting means connecting said base to said guide means for alternately cutting said tissue with a first cutting edge and with a second cutting edge longer than said first cutting edge; and
    ovoid means coupled to said cutting means for allowing said second cutting edge to extend beyond said outer wall of said base to cut a diameter of tissue larger than the diameter of said base means.

14. A rotatable atherectomy cutter as recited in claim 13, wherein said base has a generally rectangular top opening having a front rim for receiving debris, and has a sloped portion adjacent said rim of said opening to facilitate travel of said cutter through said vessel.

15. A rotatable atherectomy cutter for removing obstructive tissue from a body vessel, comprising:
a hollow cylindrical base having an outer wall;
a hollow cylindrical guide tip coaxially distanced from said base having a diameter less than the diameter of said base; and
a pair of narrow diametrically opposed blades, each having a distal end and a proximal end, each of said distal ends being connected to said tip, each of said blades establishing a first cutting edge and a second cutting edge, each of said second cutting edges being longer than each of said first cutting edges; and
an ovoid portion attached to said base and said proximal ends of said blades, said ovoid portion including a straight wall attached to said first edges of said blades to allow said second edges of said blades to extend beyond the maximum diameter of said outer wall of said base.

16. A rotatable atherectomy cutter for removing obstructive tissue from a body vessel, comprising:
a hollow cylindrical base having an outer wall;
a hollow cylindrical guide tip coaxially distanced from said base;
a pair of substantially straight diametrically opposed blades extending from said guide tip toward said base, each said blade having a first cutting edge and a second cutting edge longer than said first cutting edge; and
an ovoid portion connected to said base and having a straight wall attached to said first edges of said blades for allowing said second edges of said blades to extend beyond said outer wall of said base.

* * * * *